United States Patent
Van Davelaar

[11] Patent Number: 6,074,556
[45] Date of Patent: Jun. 13, 2000

[54] CARTRIDGE SEALING APPARATUS AND METHOD

[75] Inventor: Peter C. Van Davelaar, Maidens, Va.

[73] Assignee: Dyax Corporation, Cambridge, Mass.

[21] Appl. No.: 09/264,846

[22] Filed: Mar. 2, 1999

[51] Int. Cl.[7] .................................................. B01D 15/08
[52] U.S. Cl. ........................................ 210/198.2; 210/656
[58] Field of Search ................................ 210/635, 656, 210/659, 657, 198.2, 232, 238; 95/82; 96/101

[56] References Cited

U.S. PATENT DOCUMENTS

| | | | |
|---|---|---|---|
| 805,566 | 11/1905 | Liddle | 100/257 |
| 939,141 | 11/1909 | Kirkegaard | 100/257 |
| 2,726,707 | 12/1955 | Wellons et al. | 154/42 |
| 3,030,878 | 4/1962 | Holzer | 100/257 |
| 3,157,112 | 11/1964 | Truhon | 100/231 |
| 3,316,135 | 4/1967 | Brown et al. | 156/69 |
| 3,606,638 | 9/1971 | Putkowski | 18/16 R |
| 4,093,550 | 6/1978 | Stahl et al. | 210/198 |
| 4,250,035 | 2/1981 | McDonald et al. | 210/198.2 |
| 4,563,275 | 1/1986 | McEachern | 210/198.2 |
| 5,021,162 | 6/1991 | Sakamoto et al. | 210/635 |
| 5,137,628 | 8/1992 | Hart et al. | 210/198.2 |
| 5,193,703 | 3/1993 | Staats, III et al. | 220/203 |
| 5,227,059 | 7/1993 | Shepherd | 210/198.2 |
| 5,238,556 | 8/1993 | Shirkhan | 210/198.2 |
| 5,324,426 | 6/1994 | Joseph et al. | 210/198.2 |
| 5,462,659 | 10/1995 | Saxena et al. | 210/198.2 |
| 5,496,473 | 3/1996 | Chow | 210/198.2 |
| 5,512,168 | 4/1996 | Fetner | 210/198.2 |
| 5,582,723 | 12/1996 | Boone et al. | 210/198.2 |
| 5,601,707 | 2/1997 | Clay | 210/198.2 |
| 5,601,708 | 2/1997 | Leavesley | 210/198.2 |
| 5,651,885 | 7/1997 | Schick | 210/198.2 |
| 5,667,675 | 9/1997 | Hatch et al. | 210/198.2 |
| 5,674,455 | 10/1997 | Marchand et al. | 422/70 |
| 5,714,074 | 2/1998 | Karlsson et al. | 210/656 |
| 5,866,008 | 2/1999 | Shalon et al. | 210/656 |
| 5,893,971 | 4/1999 | Shalon | 210/198.2 |
| 5,919,361 | 7/1999 | Moran | 210/198.2 |
| 5,951,873 | 9/1999 | Shalon | 210/656 |

*Primary Examiner*—Ernest G. Therkorn
*Attorney, Agent, or Firm*—Fish & Richardson P.C.

[57] ABSTRACT

Apparatus for supporting and providing a sealable connection to an elongated flow-through cartridge, the apparatus including cartridge receiving structure for supporting a replaceable cartridge in a predetermined position, cartridge sealing structure mounted with respect to the cartridge receiving structure to be movable into an end of the cartridge to engage the cartridge at a flow structure in the cartridge, the location of the flow structure in the cartridge being variable, and a drive mechanism that automatically advances the cartridge sealing structure to seal to the cartridge at the proper location with respect to the flow structure.

17 Claims, 5 Drawing Sheets

CARTRIDGE SEALING APPARATUS AND METHOD

BACKGROUND OF THE INVENTION

The invention relates to sealing flow-through cartridges, e.g., column chromatography cartridges, of variable effective length.

Liquid column chromatography is a technique for identifying, separating, or purifying individual components in a subject sample. In employing the technique, a "stationary phase," such as a surface active powder, is packed into a chromatographic column. A "mobile phase" consisting of a carrier liquid and a sample to be identified, analyzed, or purified is passed through the column. Different compounds in the sample migrate through the column at different rates, depending, e.g., on their size and degree of attraction to the stationary phase in the column. Consequently, the different compounds in the liquid emerge from the column at different times, allowing separation of the compounds in the sample. See U.S. Pat. No. 5,601,708 to Leavesley ("Leavesley"), and U.S. Pat. No. 4,250,035 to McDonald et al., both of which are incorporated herein by reference in their entirety.

Liquid column chromatography is often carried out using disposable cylindrical cartridges. The cartridges contain the stationary phase, or media bed, bounded axially on both ends by porous plates. The ends of the cartridges are often sealed at both ends above the porous plates by sealing assemblies. Column chromatography cartridges can have media beds of different lengths, which must be taken into account in designing systems for sealing cartridges.

SUMMARY OF THE INVENTION

The invention features, in general, apparatus for supporting and providing a sealable connection to an elongated flow-through cartridge. The apparatus includes a cartridge receiving structure, a cartridge sealing structure, and a drive mechanism. The cartridge receiving structure supports a replaceable cartridge in a predetermined position. The cartridge sealing structure is mounted with respect to the cartridge receiving structure to be movable into an end of the cartridge to engage the cartridge at a flow structure in the cartridge. The location of the flow structure in the cartridge is variable from cartridge to cartridge. The drive mechanism automatically advances the cartridge sealing structure to seal to the cartridge at the proper location with respect to the flow structure.

Particular embodiments of the invention may include one or more of the following features. The cartridge is a chromatography cartridge having a media bed therein, the end of the bed being defined by a porous plate. The sealing structure seals to an internal cartridge wall. The cartridge and the sealing structure are cylindrical. There are at least two possible effective lengths, and the drive mechanism and cartridge sealing structure automatically adjust to the appropriate effective length for a cartridge placed in the receiving structure. The sealing structure is movable with respect to the cartridge to an initial seal position, and the drive mechanism further moves the cartridge sealing structure to create the seal. The sealing structure includes an elastomeric sealing ring that deforms to provide the seal as the cartridge sealing structure is moved closer to the cartridge receiving structure. The drive mechanism includes a drive rod that is movable along an axis, and the cartridge sealing structure includes a plurality of engagement structures (e.g., internal grooves) for engaging the drive rod at different locations along the axis corresponding to different variable effective lengths of the cartridge. The cartridge sealing structure has a bore that receives the drive rod, and the engagement structures are located at different positions along the bore. The drive rod has a movable structure that moves transverse to a longitudinal axis of the rod to engage an engagement structure. The drive rod has an internal pin that moves a ball to engage the engagement structure.

The cartridge receiving structure supports a plurality of cartridges in predetermined positions, a source of liquid supplies the cartridges with liquid, and a collection tray receives samples from each of the cartridges.

Embodiments of the invention may include one or more of the following advantages. The invention automatically advances the sealing structure the correct distance for sealing a cartridge of a given predetermined effective length. Without the automatic selection of the proper advancement distance, a user might have to manually adjust the apparatus between each usage, to "set" the apparatus to seal cartridges of a given predetermined effective length. If the user forgets to adjust the apparatus or improperly adjusts the apparatus, then the sealing structure might improperly seal a cartridge or break a cartridge, potentially exposing the user to harmful chemicals.

Other features and advantages of the invention will be apparent from the following description of the preferred embodiments and from the claims.

DESCRIPTION OF THE PREFERRED EMBODIMENTS

Figure 1:
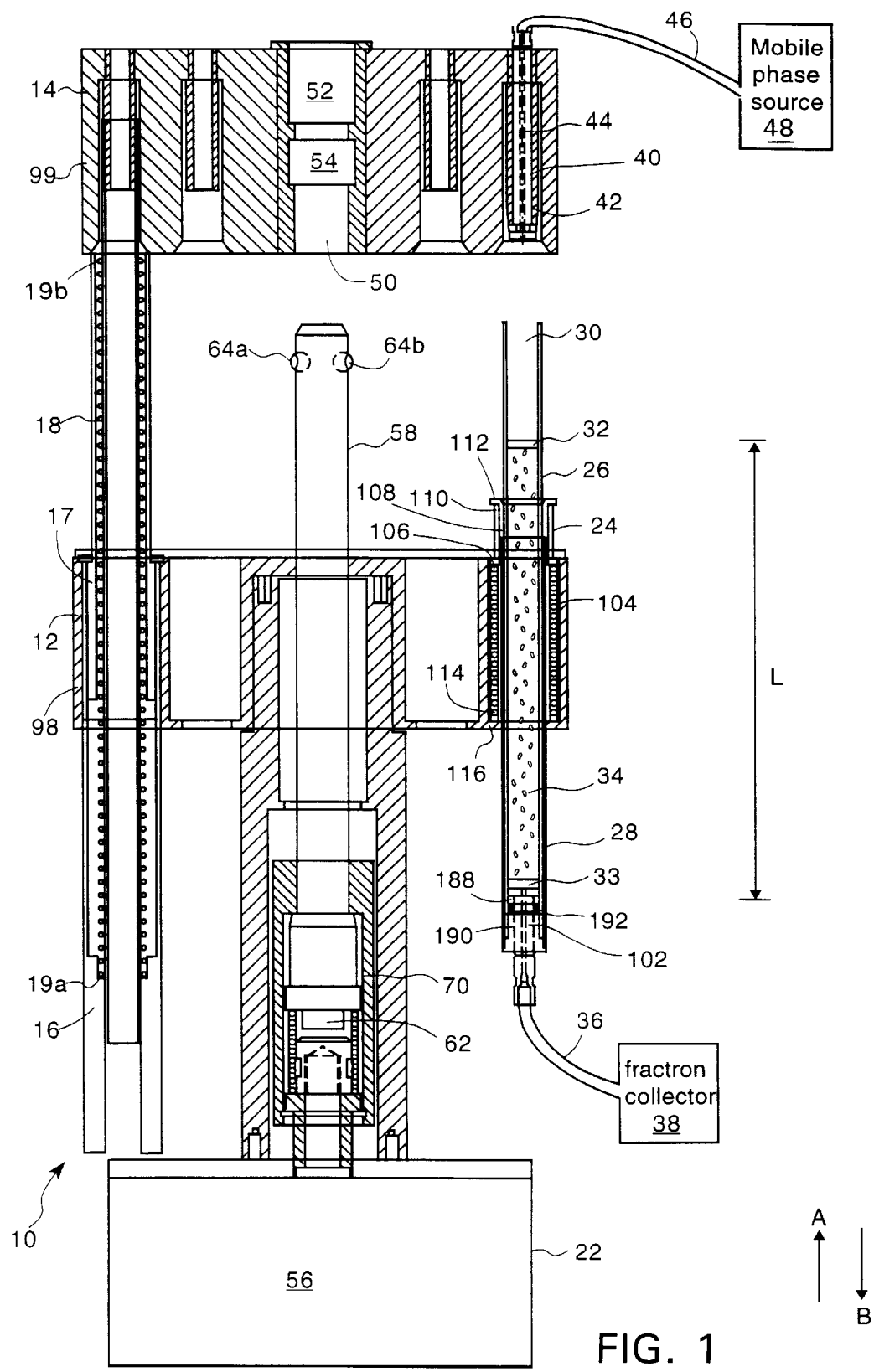
FIG. 1 is a diagrammatic elevation of an apparatus for sealing chromatography cartridges, with top and bottom components of the apparatus shown in an aligned orientation for sealing to the cartridges.
Figure 2:
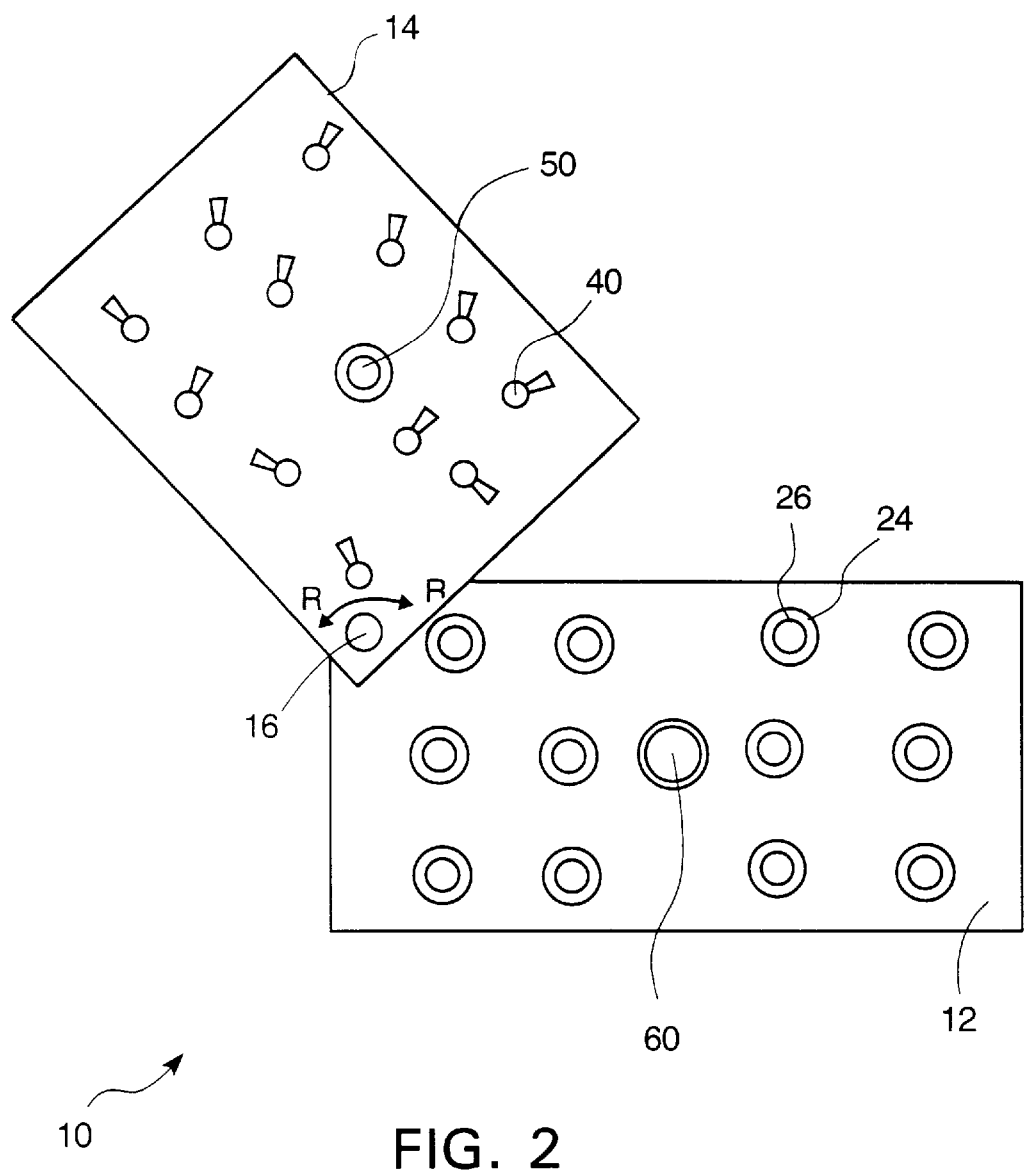
FIG. 2 is a plan view of the apparatus of FIG. 1, with a top component shown rotated with respect to a bottom component to provide access for inserting or removing cartridges.

Referring to FIGS. 1 and 2, an automated sealing apparatus 10 includes a cartridge holding unit 12, an upper sealing unit 14, a pivot tube 16, and a drive mechanism 22.

Cartridge holding unit 12 defines twelve cylindrical barrels 24 for holding twelve cylindrical column chromatography cartridges 26. Barrels 24 are arranged in three rows of four, though other arrangements and numbers of cartridges can be employed. Each barrel 24 contains a cartridge 26. In FIG. 1, only one cartridge 26 and one barrel 24 are shown.

Cartridges 26 have lower ends 28 and open upper ends 30. Upper ends 30 include upper porous plates 32, and lower 28 include lower porous plates 33. Media beds 34, the chromatographic "stationary phases," are bound between porous plates 32 and 33. Lower ends 28 connect, via outflow tubes 36 (only one tube 36 shown), to a chromatography fraction collector 38, where chromatographic samples are collected for analysis.

Sealing unit 14 includes twelve cylindrical sealing assemblies 40 (only one sealing assembly 40 shown). Sealing assemblies 40 have sealing heads 42 and define flow-through channels 44. Sealing heads 42 are sized and shaped to be inserted into upper ends 30 of cartridges 26, and to seal upper ends 30 when compressive force is applied. The structure and operation of sealing heads 42 will be described below, with reference to FIGS. 1, 5A, and 5B.

Sealing assemblies 40 are connected, via inflow tubes 46 (only one tube 46 shown), to a mobile phase source 48, which includes a 12-channel positive displacement pump to pump known volumes to each respective cartridge. The 12-channel pump is described in U.S. patent application Ser. No. 09/260,915, entitled "Pump Drive Decoupler," filed the same date as this application, and incorporated by reference herein in its entirety. Sealing unit 14 also defines a bore 50 having two cylindrical grooves, upper groove 52 and lower groove 54.

Drive mechanism 22 includes a pneumatic drive 56 and a driving rod 58. Driving rod 58 is generally cylindrical in shape, and is sized to pass through a circular hole 60 (FIG. 2) in cartridge holding unit 12, and to be insertable into bore 50 of sealing unit 14.

Rod 58 connects cartridge holding unit 12 and sealing unit 14 to drive 56. In addition, a hollow, cylindrical pivot tube 16 attaches to sealing unit 14 and passes through a hole 17 in holding unit 12. A long spring 18 is loaded into tube 16. Spring 18 engages a bottom shelf 19a of tube 16 at one end, and engages a top shelf 19b of tube 16 at a second end. Spring 18 exerts a variable force on sealing unit 14 in the direction of arrow A, and acts to stabilize sealing unit 14. In combination, the force exerted by spring 18 and friction between rod 58 and sealing unit 14 counter the gravitational force acting on sealing unit 14, allowing sealing unit 14 to remain stable with respect to rod 58 when drive 56 is inactive. Sealing unit 14 is movable axially relative to holding unit 12, and is rotatable with respect to a longitudinal axis of tube 16 and spring 18.

Figure 3:
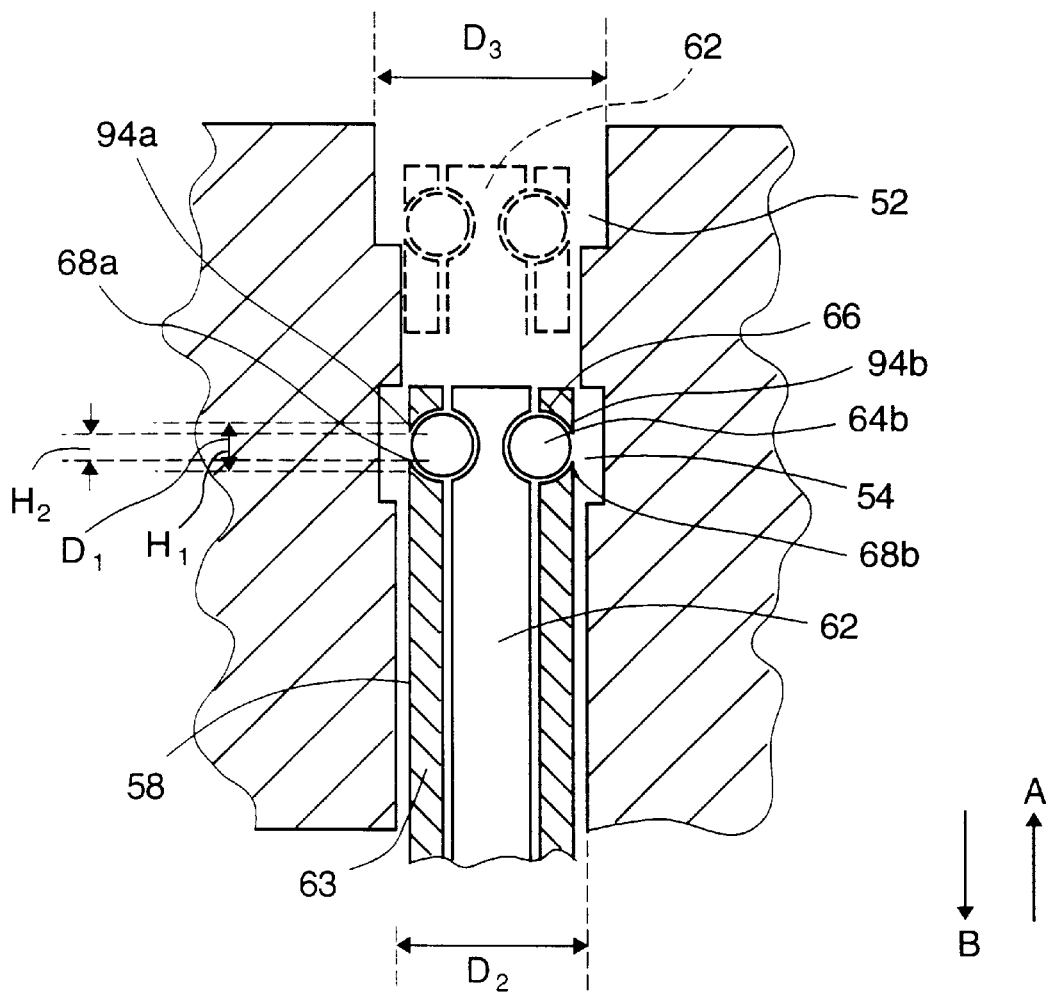
FIG. 3 is an enlarged sectional view of a drive rod and a bore of the apparatus of FIG. 1.
Figure 4:
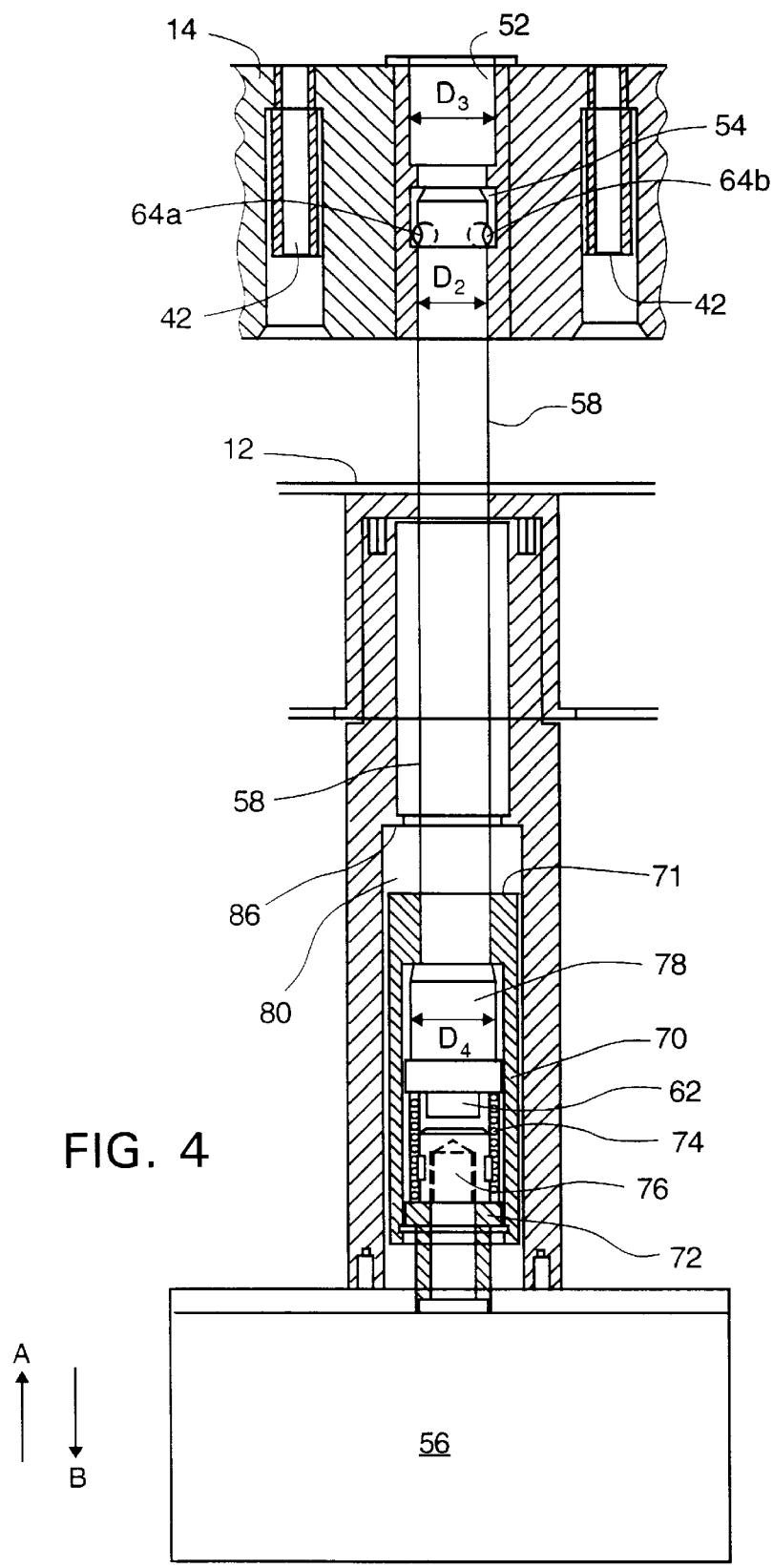
FIG. 4 is a partially sectional view of a drive rod, bore, and pneumatic drive of the apparatus of FIG. 1.

FIGS. 3 and 4 illustrate the structure of rod 58, the interaction of rod 58 with bore 50, and the connection of rod 58 to pneumatic drive 56. Referring to FIG. 3, rod 58 has an internal pin 62, a tubular outer portion 63, and engagement balls 64a, 64b. Each ball 64a, 64b has a diameter $D_1$ of, e.g., about 0.25 inches. Internal pin 62 has a circular indentation 66, and outer portion 63 has two holes 68a, 68b. Indentation 66 has a height $H_1$, and each hole 68a, 68b has an outer height $H_2$. Height $H_1$, is approximately equal to diameter $D_1$ of balls 64a, 64b, but outer height $H_2$ is less than half as large as diameter $D_1$, to prevent balls 64a, 64b from entirely leaving indentation 66 and holes 68a, 68b.

Balls 64a, 64b are movable between an internal, retracted position within indentation 66 and holes 68a, 68b, and an external, engagement position partially extending out of holes 68a, 68b into a groove 52 or 54. When balls 64a, 64b are in their retracted position, as shown in FIG. 3, the distance from the outside surface of one ball to the outside surface of the other is less than a diameter $D_2$ of bore 50. When balls 64a, 64b are in their extended engagement position, as shown in FIG. 4, the distance from the outside surface of one ball to the outside surface of the other is greater than a diameter $D_2$ of bore 50 and approximately equal to a diameter $D_3$ of grooves 52 and 54. Balls 64a, 64b are ordinarily in their extended position, as shown in FIG. 4. When pneumatic drive 56 is activated in the direction of arrow A, as discussed below, then balls 64a, 64b are forced into their retracted position.

Referring to FIG. 4, rod 58 is attached to pneumatic drive 56 by an attachment structure 70. Attachment structure 70 includes a top end 71, a platform 72, a spring 74, a punch bar 76, and a wide base 78 of bar 58. Platform 72 is connected to pneumatic drive 56, and punch bar 76 is attached to platform 72. Spring 74 connects platform 72 to wide base 78, but does not engage internal pin 62. Spring 74 is a high-load spring, having a large spring constant. Wide base 78 is connected to outer portion 63 of bar 58, but not to internal pin 62.

Attachment structure 70 resides within a bore 80. Bore 80 has an upper shelf 86 which acts as an upward stop for top end 71 of structure 70.

Figure 5A:
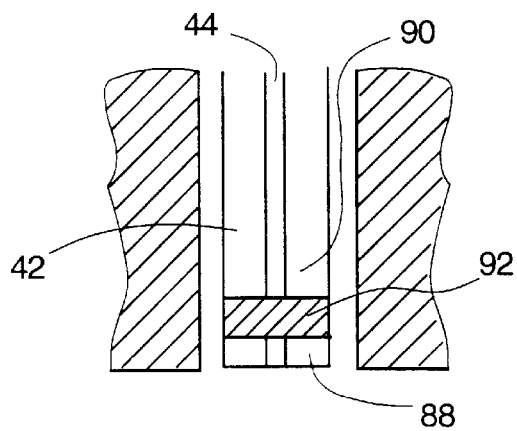
FIG. 5A is an enlarged sectional view of a chromatography cartridge and a sealing head of the apparatus of FIG. 1.
Figure 5A:
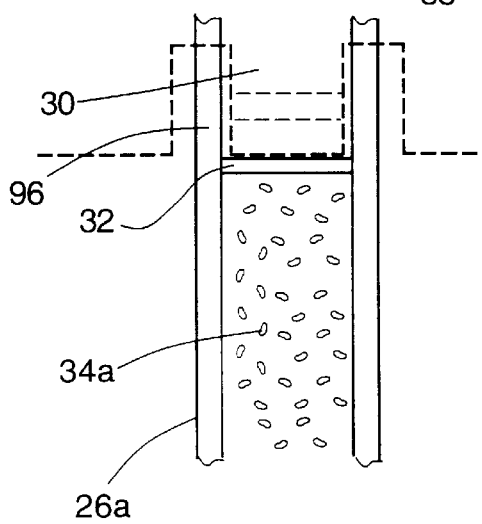
Figure 5B:
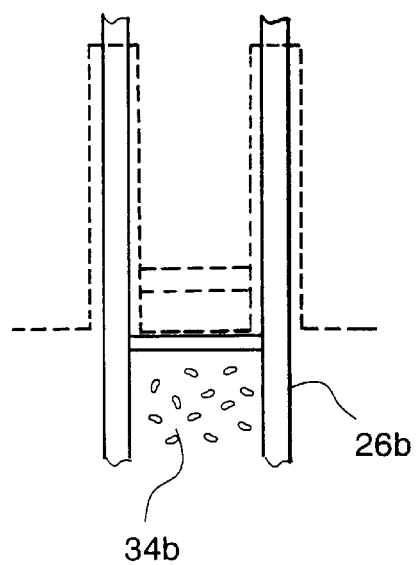
FIG. 5B is an enlarged sectional view of a chromatography cartridge and a sealing head of FIG. 1 where the cartridge has a different effective length than the cartridge of FIG. 5A.

Referring to FIGS. 5A and 5B, media beds 34 of cartridges 26 can have two different predetermined heights. The cartridges can either have high beds 34a, as shown in cartridge 26a, or low beds 34b, as shown in cartridge 26b. Cartridges having high beds can be, e.g., cartridges which include a sample module, as described in U.S. patent application Ser. No. 09/137,278, entitled "Module and Method for Introducing a Sample into a Chromatography Column," filed Aug. 20, 1998, and incorporated herein by reference in its entirety. For a single operation of apparatus 10, all cartridges 26 in barrels 28 have approximately the same effective bed height.

As shown in FIGS. 5A and 5B, each sealing head 42 has a first head piece 88, a second head piece 90, and an O-ring 92. O-ring 92 is disposed between head pieces 88 and 90. Relative movement of head piece 88 toward head piece 90 causes O-ring 92 to expand and to seal to the inside surface of the cartridge. A similar sealing arrangement is employed to seal the lower ends of the cartridges, as shown in FIG. 1.

Referring to FIG. 1, each barrel 24 holds, in addition to a cartridge 26, a lower sealing head 142 disposed within cartridge 26, abutting lower plate 33. Lower sealing heads 142 have O-rings 192 between first head pieces 188 and second head pieces 190. In addition, a spring 104 encircles each barrel 24. An upper end 106 of spring 104 is attached to a flange 108, and a lower end 114 of spring 104 engages a bottom stop 116 in cartridge holding unit 12. Flange 108 has a top end 110 which engages a lid 112 of barrel 24.

Alternatively, spring 104 can be disposed within barrel 24, below sealing head 142, or can be disposed below barrel 24. If spring 104 is below barrel 24, then upper end 106 of spring 104 would engage the bottom of the barrel 24, and the lower end would engage a stop (not shown). In addition, more than one spring can be used. For additional description of sealing apparatuses having lower sealing heads and springs, see U.S. patent application Ser. No. 09/137,264, entitled "Apparatus and Method for Sealing a Plurality of Chromatography Columns," filed Aug. 20, 1998, and incorporated herein by reference in its entirety.

Operation of apparatus 10 to seal cartridges 26 will now be described. First, a user activates pneumatic drive 56 to move upward, in the direction of arrow A, for, e.g., about a one inch upward stroke. The upward stroke first causes structure 70 to move upward until top end 71 abuts shelf 86, stopping the upward movement of structure 70. The remainder of the upward stroke then compresses spring 74, causing punch bar 76 to engage internal pin 62. Punch bar 76 pushes internal pin 62 upward, in the direction of arrow A, e.g., about 0.25 inches. The upward movement of internal pin 62 forces balls 64a, 64b from their extended positions to their retracted positions within indentation 66.

Next, the user lifts sealing unit 14 in the direction of arrow A (FIG. 1), and then rotates sealing unit 14 in the direction of arrow R (FIGS. 1–2), away from holding unit 12 to the position shown in FIG. 2. The user then loads cartridges 26 into barrels 24 of cartridge receiving unit 12 so that lower porous plates 33 rest on the tops of lower sealing heads 142 without deforming O-rings 192 at this time. Next, the user rotates sealing unit 14 into alignment with holding unit 12, and slides sealing unit 14 in the direction of arrow B, until sealing heads 42 enter cartridges 26 and abut upper porous plates 32.

When sealing unit 14 is lowered into position, as described above, drive rod 58 enters into bore 50. If cartridges 26 have the high bed height (the height of bed 34*a*), then rod 58 penetrates into lower groove 54, as shown in FIG. 3. If the cartridges 26 have the lower bed height (the height of bed 34*b*), then rod 58 penetrates into upper groove 52 of bore 50, as shown in phantom in FIG. 3.

Next, the user activates pneumatic drive 56 to move downward, in the direction of arrow B. The downward movement first decompresses spring 74, disengaging punch bar 76 from pin 62. Disengagement of punch bar 76 allows balls 64*a*, 64*b* to move from their retracted positions to their engagement positions, partially within groove 52 or groove 54. Continued downward movement of drive 56 pulls outer portion 63 of rod 58 downward. As outer portion 63 is pulled downward, top ridges 94*a*, 94*b* (FIG. 3) of holes 68*a*, 68*b* exert a downward force upon balls 64*a*, 64*b*. Balls 64*a*, 64*b* transmit the downward force to groove 52 or groove 54 of bore 50, which pushes sealing unit 14 in the direction of arrow B, toward receiving unit 12. The force exerted upon sealing unit 14 presses sealing heads 42 against porous plates 32 in cartridges 26. The compressive force against heads 42 squeezes O-rings 92 between first head pieces 88 and second head pieces 90, causing O-rings 92 to expand laterally and press against walls 96 of cartridges 26, forming circular seals. The compressive force is also transmitted through the media beds to the lower plates 33 (FIG. 6) and sealing heads 142 therebelow, causing lower O-rings 192 to also expand. Thus, when pneumatic drive 56 is activated, and a sealing head 42 presses against an upper porous plate 32, compressive forces expand both O-rings 92 and 192, sealing both ends 28, 30 of a cartridge 26. Pneumatic drive 56 pulls rod 58 with a force of, e.g., about 600 pounds. Springs 104 resist the force exerted by drive 56, reducing the net force exerted on each cartridge from, e.g., about 50 pounds to about 35 pounds. The 35 pound net force is sufficient to seal both ends 28, 30 of each cartridge 26.

Each spring 104 allows some variation in a length L of each cartridge 26. For example, length L can vary between about 6.8 and 7.1 for cartridges having high beds 34*a*, and between about 6.0 and 6.3 inches for cartridges having low beds 34*b*.

Once both ends 28, 30 of cartridges 26 have been sealed, the user can activate mobile phase source 48, beginning the flow of the mobile phase through inflow tubes 46 and flow-through channels 44, and into cartridges 26.

The components of apparatus 10 can be constructed from a variety of materials. Rod 58, including pin 62 and balls 64*a*, 64*b*, should be constructed from a durable material capable of transmitting, e.g., at least 600 pounds of force, such as a strong metal. Similarly, a housing 98 of holding unit 12 and a housing 99 of sealing unit 14 should be constructed from durable, hard materials, such as metal. Cartridges 26 can be made from high-density polyethylene, glass, stainless steel, titanium alloy, or other materials. O-ring 92 can be made from a fluorocarbon polymer or other compressible material. Sealing heads 42 can be metal or a high density polymer.

Cartridges 26 have an effective length L of, e.g., between about 5 inches and 8 inches, e.g., 6.0 inches, 6.1 inches, 6.2 inches, 6.3 inches, 6.8 inches, 6.9 inches, 7.0 inches, or 7.1 inches. In addition, apparatus 10 can be adapted for cartridges having considerably greater or smaller lengths.

Other embodiments of the invention are within the scope of the claims. For example, the number or arrangement of barrels and cartridges can be varied. More indentations can be added to bore 50, allowing apparatus 10 to automatically seal cartridges having more than two predetermined bed heights. Drives other than a pneumatic drive can be used to pull rod 58, e.g., a hydraulic drive or an electric motor drive.

The shape of rod 58 and bore 50 need not be cylindrical. Rod 58 and bore 50 can have, e.g., rectangular or triangular cross-sections. Rod 58 might have structure other than balls 64*a*, 64*b* for engaging structure in bore 50. For example, rod 58 could have a rotating member which is capable of engaging an indentation or a shelf when rotated to a first position, but can pass through bore 50 (or a differently shaped bore) when rotated to a second position. A ratchet system could also be used at the top of rod 58, permitting bore 50 to move downward with respect to rod 58 while mating angled teeth in the bore and on the rod slip past each other. The teeth would then engage at the appropriate position when rod 58 was pulled downward. The teeth would be spring biased, and could be unlatched to permit sealing unit 14 to be raised.

A sealing mechanism other than sealing head 42 can be used to seal ends 28, 30 of cartridges 26. For example, sealing structures described in U.S. application Ser. No. 09/137,019, entitled "Apparatus and Method for Making a Sealable Connection to a Chromatography Cartridge," filed Aug. 20, 1998, or the knife edge sealing mechanism described in Leavesley, supra, would suffice. U.S. application Ser. No. 09/137,019 is incorporated herein by reference in its entirety.

In addition, cartridges other than column chromatography cartridges can be sealed, so long as the cartridges have variable predetermined effective lengths.

What is claimed is:

1. Apparatus for supporting and providing a sealable connection to an elongated flow-through cartridge of variable effective length, said apparatus comprising cartridge receiving structure for supporting a replaceable cartridge in a predetermined position, cartridge sealing structure mounted with respect to said cartridge receiving structure to be movable into an end of said cartridge to engage said cartridge at a flow structure in said cartridge, the location of said flow structure in said cartridge being variable, and a drive mechanism that automatically advances said cartridge sealing structure to seal to said cartridge at the proper location with respect to said flow structure, wherein there are at least two possible effective lengths, and said drive mechanism and cartridge sealing structure automatically adjust to the appropriate effective length for a cartridge placed in said receiving structure.

2. The apparatus of claim 1 wherein said cartridge is a chromatography cartridge having a media bed therein, and said location is at an end of said bed.

3. The apparatus of claim 2 wherein said end of said bed is defined by a porous plate, and said location is at said porous plate.

4. The apparatus of claim 1 wherein said sealing structure seals to an internal cartridge wall.

5. The apparatus of claim 1 wherein said cartridge and said sealing structure are cylindrical.

6. The apparatus of claim 1 wherein said sealing structure is movable with respect to said cartridge to an initial seal position, and said drive mechanism further moves said cartridge sealing structure to create said seal.

7. The apparatus of claim 6, wherein said sealing structure includes an elastomeric sealing ring that deforms to provide said seal as said cartridge sealing structure is moved closer to said cartridge receiving structure.

8. The apparatus of claim 1 wherein said drive mechanism includes a drive rod that is movable along an axis, and said cartridge sealing structure includes a plurality of engagement structures for engaging said drive rod at different locations along said axis corresponding to different variable effective lengths.

9. The apparatus of claim 8 wherein said cartridge sealing structure has a bore that receives said drive rod, and said engagement structures are located at different positions along said bore.

10. The apparatus of claim 9 wherein said rod has a movable structure that moves transverse to a longitudinal axis of said rod to engage a said engagement structure.

11. The apparatus of claim 10 wherein said rod has an actuator that moves said movable structure.

12. The apparatus of claim 11 wherein said actuator comprises an internal pin, and said movable structure comprises a ball that is moved in a transverse direction when said internal pin moves along said longitudinal axis.

13. The apparatus of claim 8 wherein said drive mechanism includes a driver that moves said drive rod along its axis in order to move said cartridge sealing structure with respect to said cartridge receiving structure.

14. The apparatus of claim 1, 3, 8, or 9 wherein said cartridge receiving structure supports a plurality of cartridges in predetermined positions.

15. The apparatus of claim 1 or 8 wherein said cartridge receiving structure supports a plurality of cartridges in predetermined positions, and wherein said cartridge sealing structure is movable in a transverse direction with respect to said cartridge receiving structure to permit placing said cartridges in said receiving structure, and is movable in a direction toward said cartridge sealing structure to provide said seal.

16. The apparatus of claim 1 wherein said cartridge receiving structure supports a plurality of cartridges in predetermined positions, and further comprising a source of liquid that supplies said cartridges with liquid.

17. The apparatus of claim 16 further comprising a collection tray that receives samples from each of said cartridges.

* * * * *